(12) United States Patent
Pantano et al.

(10) Patent No.: US 6,916,541 B2
(45) Date of Patent: Jul. 12, 2005

(54) MODIFIED SUBSTRATES FOR THE ATTACHMENT OF BIOMOLECULES

(75) Inventors: Carlo G. Pantano, Pennsylvania Furnace, PA (US); Ezz Metwalli, State College, PA (US); Samuel Conzone, Clarks Green, PA (US); Dan Haines, Moscow, PA (US)

(73) Assignee: Penn State Research Foundation, University Park, PA (US)

( * ) Notice: Subject to any disclaimer, the term of this patent is extended or adjusted under 35 U.S.C. 154(b) by 303 days.

(21) Appl. No.: 09/947,923

(22) Filed: Sep. 7, 2001

(65) Prior Publication Data

US 2003/0054176 A1 Mar. 20, 2003

(51) Int. Cl.[7] .......................... B32B 17/06; B05D 3/02; C12Q 1/68
(52) U.S. Cl. ....................... 428/429; 428/446; 428/447; 428/448; 427/387; 427/452; 427/489; 427/503; 427/515; 427/527; 427/574; 427/585; 536/24.3; 435/6
(58) Field of Search ................................ 428/428, 429, 428/446, 447, 448; 435/6; 536/24.3; 427/452, 489, 503, 515, 527, 574, 585, 387

(56) References Cited

U.S. PATENT DOCUMENTS

| | | | |
|---|---|---|---|
| 4,776,869 A | 10/1988 | Offenbacher | |
| 4,994,373 A | 2/1991 | Stavrianopoulos et al. | |
| 5,077,210 A | 12/1991 | Eiger | |
| 5,418,136 A | * 5/1995 | Miller et al. | 435/5 |
| 5,474,796 A | 12/1995 | Brennan | |
| 5,541,057 A | * 7/1996 | Bogart et al. | 435/5 |
| 5,624,711 A | 4/1997 | Sundberg | |
| 5,677,126 A | 10/1997 | Bensimon | |
| 5,688,642 A | 11/1997 | Chrissy | |
| 5,760,130 A | 6/1998 | Johnston | |
| 5,919,626 A | 7/1999 | Shi et al. | |
| 5,959,098 A | * 9/1999 | Goldberg et al. | 536/25.3 |
| 6,258,454 B1 | 7/2001 | Lefkowitz | |
| 6,262,216 B1 | 7/2001 | McGall | 528/10 |
| 6,306,589 B1 | * 10/2001 | Muller et al. | 435/6 |
| 6,307,042 B1 | 10/2001 | Goldberg | |
| 6,309,831 B1 | 10/2001 | Goldberg | |
| 6,319,674 B1 | 11/2001 | Fulcrand | |
| 6,410,675 B2 | 6/2002 | McGall et al. | 528/10 |
| 6,432,191 B2 | * 8/2002 | Schutt | 106/287.13 |
| 2001/0044106 A1 | 11/2001 | Henderson | |
| 2003/0022216 A1 | * 1/2003 | Mao et al. | 435/6 |

FOREIGN PATENT DOCUMENTS

| | | |
|---|---|---|
| EP | 0947246 A1 | 10/1999 |
| EP | 1223149 A1 | 7/2002 |
| WO | 98/04652 A1 | 2/1998 |
| WO | 99/40038 | 8/1999 |
| WO | 01/70641 A1 | 9/2001 |

OTHER PUBLICATIONS

Chrissy et al. "Covalent attachment of synthetic DNA to self–assembled monolayers," Nucleic Acid Research 1996, vol. 24, No. 15, 3031–3039.

Chrissey et al. "Selective Attachment of Synthetic DNA to Self–Assembled Monolayer Functionalized Surfaces" Mat. Res. Soc. Symp. Proc. vol. 330, 1994, pp. 179–184.

Lamture et al. "Direct detection of nucleic acid hybridization on the surface of a charge coupled device" Nucleic Acid Research, 1994, vol. 22, No. 11 2121–2125.

B.J. Spargo et al., "Spatially controlled adhesion, spreading, and differentiation of endothelial cells on self–assembled molecular monolayers", Proc. Natl. Acad. Sci. USA, vol. 91, pp. 11070–11074, Nov. 1994, Cell Biology, XP–002103614.

* cited by examiner

Primary Examiner—Jeffrey B. Robertson
(74) Attorney, Agent, or Firm—Millen, White, Zelano, Branigan, P.C.

(57) ABSTRACT

The present invention relates to a substrate for attachment of biomolecules. The substrate is coated with a multiamino organosilane. If desired, the substrate can be further modified prior to coating with a multiamino organosilane. Optional surface modifications include coating the substrate with $SiO_2$ or leaching with acid to form a $SiO_2$ rich layer. DNA, nucleic acids, or any bimolecules can be attached to the coated substrates of the invention. Although a variety of substrates are contemplated, the preferred substrate is a low self-fluorescent glass.

27 Claims, 5 Drawing Sheets

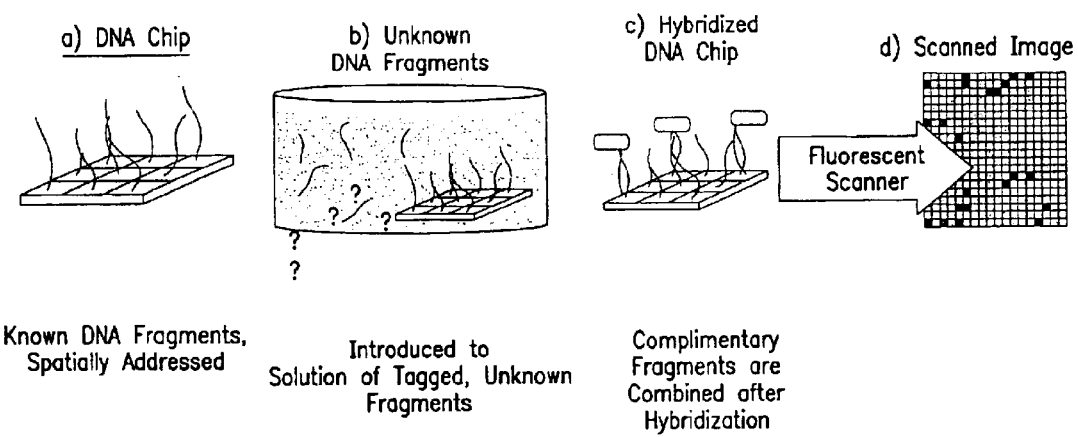

Figure 2:
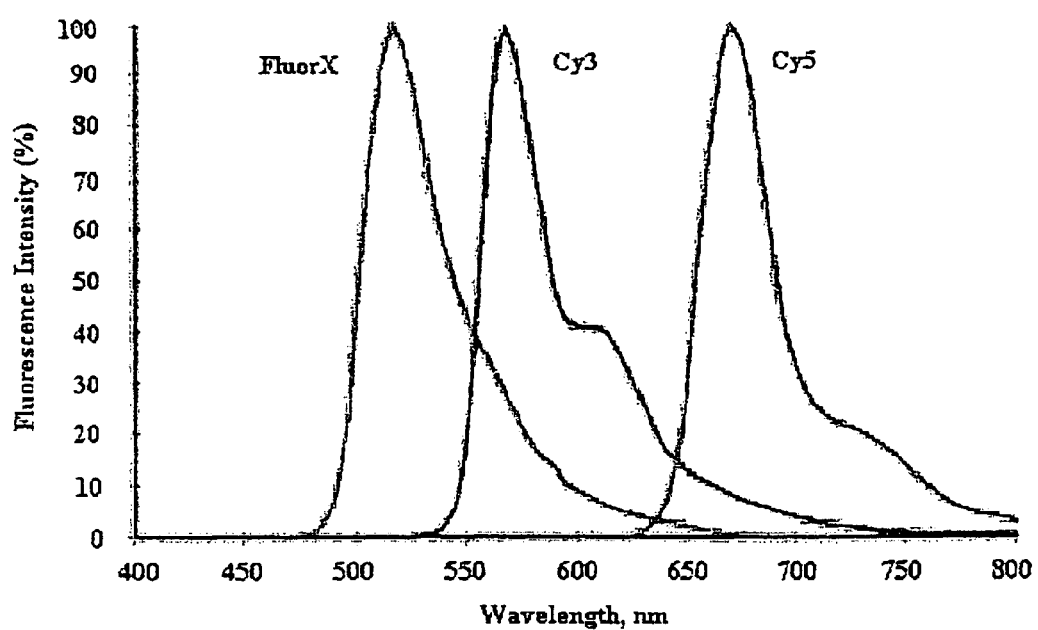

Pictorial representation of the typical steps that are involved with a DNA microarray experiment. A DNA chip containing known DNA fragments (probes) at known locations(a) is introduced to a solution containing fluorescently-tagged, unknown DNA(targets)(b). hybridizationn occurs between complimentary DNA fragments(c), and a scanner is then used to determine the identity and quantity of unknown DNA(d).

FIG. 1

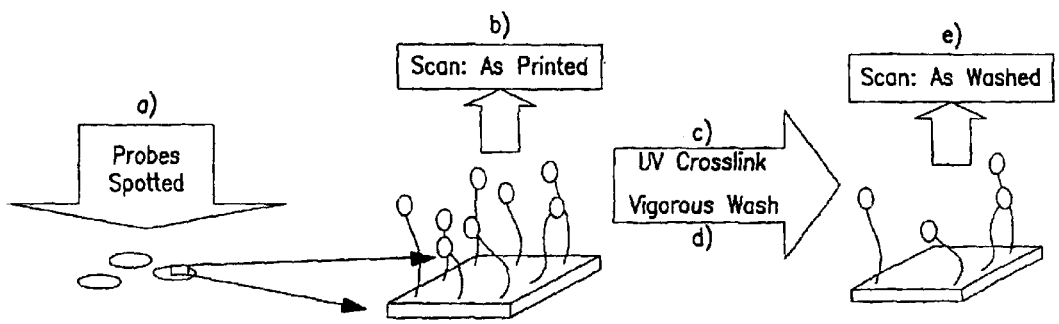

Pictorial representation of a typical DNA retention experiment, which includes a) spotting of tagged DNA probes onto a glass surface in triplicate, b) scanning the fluorescent intensity of the tagged DNA probes in the as-printed state, c) UV crosslinking and/or heat to achieve covalent bonding between the DNA probes and the coated substrate, d) vigorous washing with a detergent and boiling $H_2O$, and e) final scanning to determine the percent of DNA probes that were retained after the vigorous washing step.

FIG. 4

US 6,916,541 B2

MODIFIED SUBSTRATES FOR THE ATTACHMENT OF BIOMOLECULES

The present invention relates generally to substrates suitable for the attachment of biomolecules and more particularly to coated, low self-fluorescent glass substrates suitable for the attachment of biomolecules such as nucleic acid molecules, including oligonucleotides and proteins. The invention also relates to a reliable and robust method for attaching such biomolecules.

SUMMARY OF THE INVENTION

The present invention relates to a substrate for covalent attachment of biomolecules. The substrate is coated with a multiamino organosilane. If desired, the substrate can be further modified prior to coating with such a multiamino organosilane.

Optional surface modifications include coating the substrate with $SiO_2$ or leaching with acid to form a $SiO_2$ layer, which may or may not possess microporosity depending on the process. As would be known to a skilled worker, both surfaces are included. The $SiO_2$ coating is preferably applied to the substrate by chemical vapor deposition, sputtering, or dip coating, but other techniques can be used. The $SiO_2$ coating can be a sol gel coating derived from tetraethylorthosilicate, tetramethylorthosilicate, or a sol gel coating derived from sodium silicate solution, alkali silicate solution, alkaline earth silicate solution or a colloidal silica suspension. In yet another aspect of the invention a substrate can be etched with a strong acid such as HCl, HF, $HNO_3$, $H_2SO_4$, prior to coating with a multiamino organosilane. The multiamino organosilane reagents are then covalently bound to the etched surface of a low self-fluorescent substrate.

DNA, unmodified nucleic acids, antibodies, antigens, proteins, oligonucleotides, or any biomolecules can be attached to the coated substrates of the invention. Although a variety of substrates are contemplated, the preferred substrate is a low self-fluorescent glass, for example borosilicate or soda lime silicate glass among others. The multiamino organosilane is preferably a trimethoxysiylpropyl-diethylenetriamine (DETA).

The invention also relates to a method of attaching biomolecules to a substrate. The substrate is first optionally coated with $SiO_2$ or leached with acid, and subsequently coated with a multiamino organo silane such as N-(2-aminoethyl)-3-aminopropyltrimethoxysilane (EDA), or (aminoethyl aminomethyl)phenethyltrimethoxysilane (PEDA). Most preferably, the multiamino organosilane is trimethoxysilylpropyl-diethylenetriamine (DETA).

The preferred use of the present invention is to covalently or non-covalently immobilize a controlled density of biomolecules, preferably functional nucleic acid molecules and particularly nucleic acid oligomers, onto the coated substrate. The present invention thus can provide sensors, biosurfaces or biomaterials for a variety of biological, analytical, electrical or optical uses. The coated substrates can also be used as "adhesive scaffolds" upon which tissue engineering can be conducted.

Thus, in general, the coated substrates of the present invention can be used in processes for detecting and/or assaying a molecule with biological activity in a sample, characterized in that a coated substrate as described above, on which a molecule with biological activity capable of recognizing the sample molecule becomes attached, is used, the detection or assay can be carried out using a reagent, fluorescent or otherwise, which detects the presence of the attached molecule.

The aminized glass substrates of the present invention provide exceptionally low self-fluorescence with DNA retention that is preferably greater than 50% improved over that obtained using traditional aminopropyl silane, such as APS coatings on borosilicate or soda lime silicate glass. Unlike traditional techniques, the present invention does not require the use of expensive crosslinking agents, which are typically very difficult to use and quite sensitive to air and humidity.

A more complete appreciation of the invention will be readily obtained by reference to the accompanying drawings, wherein:

FIG. 1 is a pictorial representation of the typical steps that are involved when DNA (probes) at known locations on a solid substrate (a) is introduced to a solution containing fluorescently tagged, unknown DNA (targets), (b) hybridization occurs between complimentary DNA fragments, (c) and a scanner is then used to determine the identity and quantity of unknown DNA (d). The substrate used for such a DNA microarray experiment could be the multiamino organosilane coated substrate of the present invention.

FIG. 2 depicts an emission spectra showing the fluorescent intensity of common fluorescent dyes. Excitation and emission data for Cy3™ and Cy5™ fluorescent dies, followed by plots of the emission spectra for Cy3™, Cy5™ and FluorX™.

Figure 3:
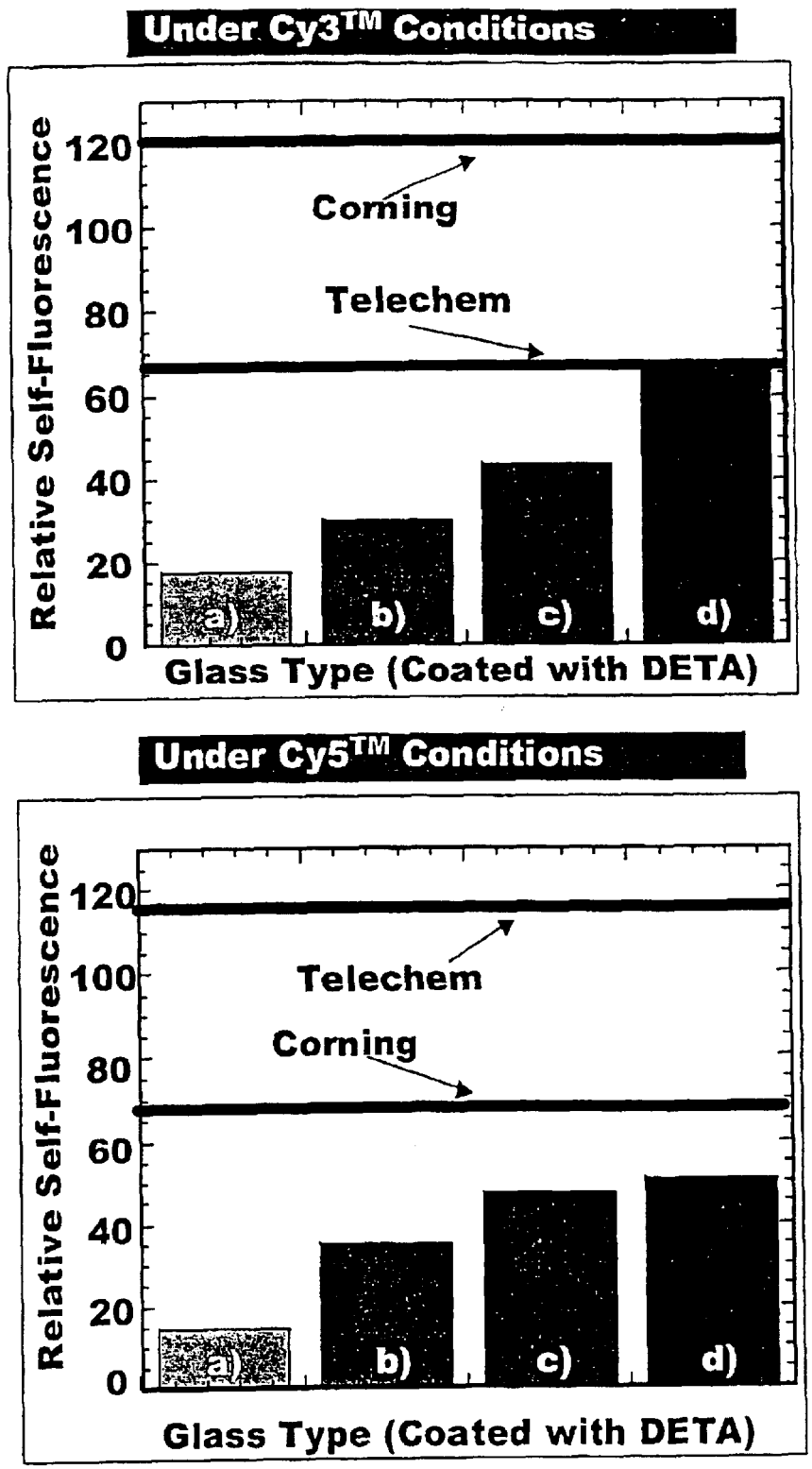

FIG. 3 shows self-fluorescence for various DETA-coated glasses measured under Cy3™ (top) and Cy5™ (bottom) excitation and emission conditions. Data obtained from conmercially available Corning CMT Gaps and Telechem Super Amine substrates are also shown. All relative fluorescence values were corrected for thickness by dividing the output value from the Axon GenePix scanner by the thickness of the respective substrate in mm. Nominal standard deviations are ±4% ( nominal thickness of $SiO_2$=2.3 mm, borosilicate 1=1.2 mm, borosilicate 2=1.1 mm, borosilicate 3=1.1 mm, Corning CMT=1.0 mm, Telechem=1.0 mm).

FIG. 4 is a pictorial representation of a typical DNA retention experiment, which includes a) spotting of tagged DNA probes onto a glass surface in triplicate, b) scanning the fluorescent intensity of the tagged DNA probes in the as-printed state, c) UV crosslinking and/or heat to achieve covalent bonding between the DNA probes and the coated substrate, d) vigorous washing with a detergent and boiling $H_2O$, and e) final scanning to determine the percent of DNA probes that were retained after the vigorous washing step.

Figure 5:
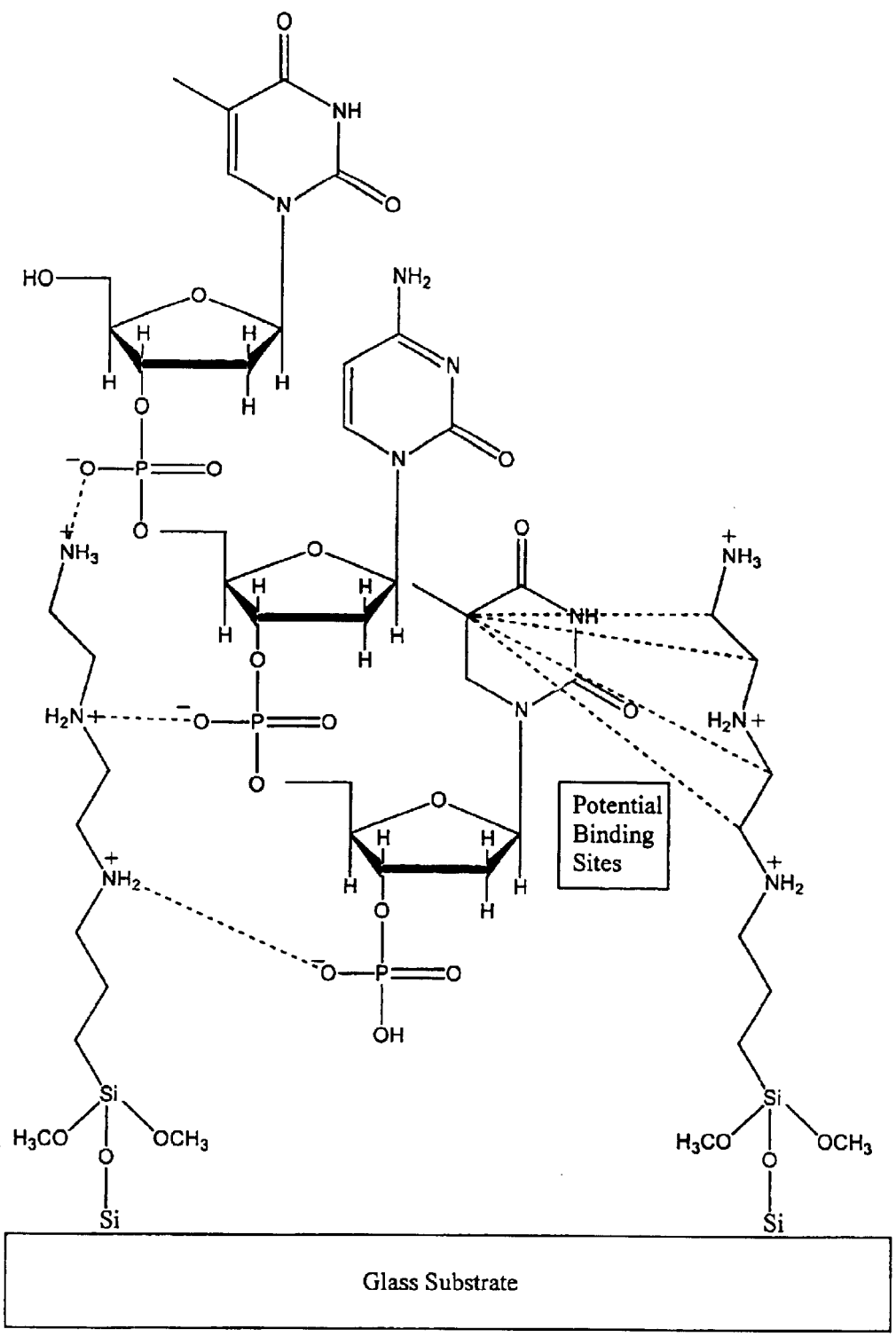

FIG. 5 shows the ionic and covalent attachment of a 3-mer oligonucleotide to DETA molecules on a glass surface. Ionic bonding between the phosphate backbone of the oligonucleotide and amine groups is depicted on the left, while non-specific covalent bonding between the thymidine residue on the oligonucleotide and the alkyl group of the DETA molecule is shown on the right.

Biomolecules, particularly nucleic acids, have been immobilized on a variety of solid surfaces, for a number of known applications, including DNA and RNA oligomer synthesis; separation of desired target nucleic acids from mixtures of nucleic acids including RNA; conducting sequence-specific hybridizations to detect desired genetic targets (DNA or RNA); creating affinity columns for mRNA isolation; quantification and purification of PCR reactions; characterization of nucleic acids by AFM and STM; for sequence determination of unknown DNAs, such as the human genome. A number of methods have been employed to attach biomolecules to substrates. There are numerous patents and patent applications, which describe arrays of oligonucleotides and methods for their fabrication, and a variety of substrates for DNA immobilization, including polymeric membranes (nylon, nitrocellulose), magnetic particles, mica, glass or silica, gold, cellulose, and polystyrene, etc. They include: U.S. Pat. Nos. 5,077,210; 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; 5,677,126; 5,688,642; 5,700,637; 5,744,305; 5,760,130; 5,837,832; 5,843,655; 5,861,242; 5,874,974; 5,885,837; 5,919,626; PCT/US98/26245; WO 93/17126; WO 95/11995; WO 95/35505; EP 742 287; and EP 799 897. There are numerous patents and patent applications describing methods of using arrays in various applications, they include: U.S. Pat. Nos. 5,143,854; 5,288,644; 5,324,633; 5,432,049; 5,470,710; 5,492,806; 5,510,270; 5,525,464; 5,547,839; 5,580,732; 5,661,028; 5,848,659; 5,874,219;WO 95/21265; WO 96/31622; WO 97/10365; WO 97/27317; EP 373203; and EP 785 280. The techniques and uses in these documents are all applicable herein.

The substrates to be modified for use in the methods and products of the present invention include materials which have or can be modified to have surface hydroxyl groups which can react with silanes. Suitable substrates are preferably inorganic materials, including but not limited to silicon, glass, silica, diamond, quartz, alumina, silicon nitride, platinum, gold, aluminum, tungsten, titanium, various other metals and various other ceramics. Alternatively, polymeric materials such as polyesters, polyamides, polyimides, acrylics, polyethers, polysulfones, fluoropolymers, etc. may be used as suitable organic substrates. The substrate used may be provided in any suitable form, such as slides, wafers, fibers, beads, particles, strands, precipitates, gels, sheets, tubing, spheres, containers, capillaries, pads, slices, films, plates, slides, etc. The substrate may have any convenient shape, such as that of a disc, square, sphere, circle, etc. The support can further be fashioned as a bead, dipstick, test tube, pin, membrane, channel, capillary tube, column, or as an array of pins or glass fibers.

Although the substrate may be made of a variety of either flexible or rigid, glass or plastic solid supports, glass is the preferred solid substrate. Additionally, the substrate may also be a coverslip, a capillary tube, a glass bead, a channel, a glass plate, a quartz wafer, a nylon or nitrocellulose membrane or a silicon wafer. The solid support can also be plastic, preferably in the form of a 96-well plate or 384-well plate. Preferably, the plastic support is a form of polystyrene plastic.

As mentioned above, the array is present on either a flexible or rigid substrate. A flexible substrate is capable of being bent, folded or similarly manipulated without breakage. Examples of solid materials which are flexible solid supports with respect to the present invention include membranes, e.g., nylon, flexible plastic films, and the like. By "rigid" is meant that the support is solid and does not readily bend, i.e., the support is not flexible. As such, the rigid substrates for use in bioarrays are sufficient to provide physical support and structure to the associated biomolecules such as oligonucleotides and/or polynucleotides present thereon under the assay conditions in which the array is employed, particularly under high throughput handling conditions.

The substrate and its surface are also chosen to provide appropriate optical characteristics. In a preferred embodiment, the substrate is a low self-fluorescent glass, or a pure $SiO_2$ glass, most preferably, a low self-fluorescent borosilicate or soda-lime glass. However, the substrate may be a $SiO_2$ coated polymer such as (poly) tetrafluoroethylene, (poly)vinylidenedifluoride, polystyrene, polycarbonate, etc., or combinations thereof.

If the chosen substrate is glass, it is desirable to clean the glass substrate prior to coating according to the following general glass cleaning protocol: Agitate the glass slides in 1–70 wt % $NaOH_{(aq)}$ solution for 0.1 to 24 hrs and then sonicate in doubly distilled (dd) $H_2O$ for 0.1 to 24 hrs. Further agitate the slides in 0.1–70 wt % $HCl_{(aq)}$ for 0.1 to 24 hrs and sonicate in doubly distilled $H_2O$ for 0.1 to 24 hrs, after which, the slides are shaken in ultra-pure, low residue methanol for 0.1 to 24 hrs. The various cleaning steps can be conducted from about 4 to 95° C.

The self (background) fluorescence of a DNA microarray must be minimized, since fluorescent scanning is often the analytical technique used to determine the outcome of a DNA microarray assay. The main contribution to self-fluorescence is generally the solid support, which is often comprised of glass. The compositions of several suitable low self-fluorescent glass substrates are listed in example II. By "low fluorescence" herein is typically meant less than 70 relative self fluorescent units (emission quata) when all background readings are scanned at 100% laser power at constant sensitivity and normalized for substrate thickness (photomultiplier tube gain PMT=700 axon using a GenePix Pro 3 scanner and software package).

Most preferably the glass substrate is a low self-fluorescence multi-component oxide silicate glass. Suitable such glasses include borosilicate 1, borosilicate 2, borosilicate 3 and soda-lime silicate 1 (Example II) or a low self-fluorescent synthetic fused silica. These low self-fluorescent glasses are obtained using extremely pure raw materials in the melting process and thus avoid the incorporation of problematic transition metal ions and rare earth metal ions into the glass structure. Most preferably, the low self-fluorescence solid support is fashioned as a microscope slide. Typical slides have a thickness of about 1 mm and are 25 mm wide×75 mm long.

If desired, an optional coating step can be performed after the substrate is cleaned, whereby the glass or other surface is coated with $SiO_2$. This coating step could be accomplished by the chemical vapor deposition of $SiO_2$, the sputtering of $SiO_2$, mist deposition with an aerosol, and/or the liquid phase deposition or dip coating of $SiO_2$ via a sol gel technique, ion beam deposition, flame hydrolysis deposition, laser pyrolysis deposition, liquid phase deposition, electron beam deposition, plasma arc deposition or flash evaporation deposition. The sol gel coatings can be deposited from both acidic and basic solutions to influence the pore size and specific surface area of the deposited silica. The drying conditions can be varied from air to nitrogen to influence carbomide formation.

The preferred $SiO_2$ coating is a sol gel coating derived from tetraethylorthosilicate (TEOS), tetramethylorthosilicate, or a sol gel coating derived from sodium silicate solution, alkali silicate solution, alkaline earth silicate solution or a colloidal silica suspension. Such modification layers, when present, will generally range in thickness from a monomolecular thickness to about several hundred microns.

In addition to modifying the surface of glass substrates with a coating of $SiO_2$, leaching with a strong acid provides yet another method of forming a $SiO_2$ rich layer on low self-fluorescent glass substrates.

This is typically achieved by using an aqueous solution, which contains a strong acid such as HCl, HF, $HNO_3$, or $H_2SO_4$ at a temperature ranging from 4 to 100° C. The acid will leach borate and alkali constituents from the glass surface, generally leaving behind a hydrated, nanoporous silicic acid gel at the surface. This surface is subsequently heat treated at a temperature of about 60–400 C to yield a nanopourous $SiO_2$. By "nanopourous" herein is typically meant a having pores of less than 250 nm. Afterwards, the multi amino organosilane reagents are covalently bound to the etched or $SiO_2$ coated surface of the low self-fluorescent substrate. In an alternative embodiment amino silane reagents such as APS, are bound to the etched or $SiO_2$ coated surface of the low self-fluorescent substrate. The etched or $SiO_2$ coated surfaces thus obtained have improved biomolecule adhesion.

The amino silanes useful for the invention can bind to the substrate's hydroxyl groups or in an alternative embodiment to the hydroxyl groups of the etched or $SiO_2$ coated substrates mentioned above, and include a wide variety of silanes, preferably amino silanes such as aminopropyl trialkoxy silane or aminobutyldimethylmethoxysilane, and most preferably multiamino silanes having more than one amine group. The multiamino organosilane linker molecules are preferably of sufficient length to permit oligonucleotides, polynucleotides and/or other biomolecules to interact freely with the functional groups exposed at the surface of the coated substrates. Traditionally used aminopropylsilane (APS) linker molecules contain only one amine group, only one propyl group and are about 455 pm in length, while the DETA molecule, which is a preferred multiamino organosilane of the present invention is three times longer at about 1351 pm in length. Suitable linker molecules may be, for example, multiamino alkyl monoalkoxy silane, multiamino alkyl dialkoxy silane, and/or a multiamino alkyl trialkoxy silane. Also suitable are multiamino organosilanes such as trimethoxysilylpropyl-diethylenetriamine (DETA), N-(2-aminoethyl)-3-aminopropyltrimethoxysilane (EDA), and/or (aminoethyl aminomethyl)phenethyltrimethoxysilane (PEDA).

A multiamino organo silane coating such as DETA differs from traditional APS coatings that are commonly used for DNA microarray applications. The DETA molecule contains three amine groups (one primary amine, and two secondary amines). Each of the three amine groups in DETA can become protonated in an aqueous solution, thus resulting in a DETA molecule that has a formal (+3) charge. The first step in DNA adhesion to an amine-coated surface is electrostatic attraction, and this (+3) charge theoretically should be at least three times as effective at attracting a negatively charged nucleic acid probe than, e.g., a formal (+1) charge on an APS molecule. The DETA linker arm, where a linker arm is defined as the chemical structure that exists between the silicon atom and the nitrogen from the primary amine, see FIG. 5, contains a propyl group, two secondary amines and two ethyl groups. Thus, the DETA linker arm is nearly 3 times longer than that for, e.g., the conventional APS. This longer linker arm manifests itself in the form of a more compliant coating that will better allow a long (>25 nucleotide) nucleic acid probe to configure itself in such a way that covalent bonding can occur. Further, when covalent bonding between a nucleic acid probe and the coating is catalyzed using UV light and/or heat (FIG. 5), there are twice as many alkyl groups available for bonding in the DETA molecule as there are with APS. Preferred linker arm lengths are greater than about $455_{pm}$. A preferred number of amino groups is 2–5, but up to 10 are useful, or more.

Coating of the multiamino organosilane is performed either directly onto a substrate, onto an optionally $SiO_2$ coated substrate, or onto an optionally acid leached substrate. Such modification layers, when present, will generally range in thickness from a monomolecular thickness to about several hundred microns.

A typical protocol for coating using one of the preferred multiamino organosilanes can be accomplished by shaking a clean substrate in DETA (0.1 to 20 wt %) solution for 15 min. Preferably the DETA is from 1–10 wt % and most preferably from 4 to 6%. The solution can contain 5 to 99.9 wt % of $H_2O$ and 5 to 99.9 wt % of an organic solvent such as acetone, toluene, isopropanol, methanol, ether or ethanol. Acetic acid may be used to adjust pH in an aqueous solution, but the DETA solution is generally maintained at a pH of 7–14 and most preferably at a pH of 9–11 for glass substrate coating applications. After dip coating, the substrates are then shaken in ultra-pure, low residue methanol, ethanol, and/or isopropanol again for about 0.1 to 24 hours and rinsed well with double distilled $H_2O$ for about 0.1 to 24 hours. After rinsing the substrates are spin dried for about 5 min. at 1000 rpm (Class-100 clean room is optional) and heat-treated at a temperature ranging from 70 to 250 C for 0.1 to 24 hours. Preferably at a temperature ranging from 100–140 C, and most preferably at a temperature ranging from 110–130 C (Class-100 clean room is optional). The coated substrates can be stored in a vacuum desiccator.

The DETA coated surfaces thus obtained are useful for attaching molecules having biological activity, i.e, "biomolecules" such as proteins, nucleic acids, lipids, polysaccharides, RNAs, DNAs and derivatives thereof. A nucleic acid is a covalently linked sequence of nucleotides and includes "polynucleotides," a nucleic acid containing a sequence that is greater than about 100 nucleotides in length; oligonucleotides, a short polynucleotide or a portion of a polynucleotide; and SNPs, (single nucleotide polymorphisms) which are variations from the most frequently occurring base at a particular nucleic acid position. As used herein, the term "target nucleic acid" or "nucleic acid target" refers to a particular nucleic acid sequence of interest. Thus, the "target" can exist in the presence of other nucleic acid molecules or within a larger nucleic acid molecule. Among the proteins, are included enzymes, antigens and antibodies, ligands, receptors, as well as the derivatives of these compounds, etc.

All RNAs and DNAs are included, e.g., alpha, beta, derivatives as well as thio derivatives and mixed compounds such as PNAs. Mixed compounds such as glycoproteins, glycopeptides and lipopolysaccharides for example, or alternatively other elements such as viruses, cells, or chemical compounds such as biotin, can also be attached.

Thus, in general, the coated substrates of the present invention can be used in processes for detecting and/or assaying a molecule with biological activity in a sample, characterized in that a coated substrate as described above, on which a molecule with biological activity capable of recognizing the sample molecule becomes attached, is used, and in that the detection or assay are carried out using a reagent, fluorescent or otherwise, which detects the presence of the attached molecule. The activity of the biomolecule may be maintained after immobilization to the surface. For example, immobilized DNA or RNA probes may retain their ability to hybridize to a complementary DNA or RNA molecule in a sequence-specific manner, or to function as primers for nucleic acid amplification techniques.

Pin spotting and ink jet printing are the most common techniques used to place small volumes (spots) of solution, which contain known DNA fragments (probes), onto a solid support. An ideal solid support for DNA microarray applications would have zero self-fluorescence, and would form a strong chemical (covalent) bond with the probes that are pin spotted or ink jet printed onto the glass surface. After covalent bonding is achieved, the probe/coated substrate interactions should be strong enough to survive washing with mild detergents and/or immersion in boiling $H_2O$. Such strong covalent bonding is desirable for DNA microarray applications, since it is often vital that the probes are immobilized on the solid support, and that they remain immobilized at a known location after various hybridization and cleaning steps.

With an automated delivery system, such as a Hamilton robot (e.g., Hamilton 2200 pipeting robot (Hamilton, Inc., Reno, Nev.)) or ink-jet printing method, it is possible to form a complex array of nucleic acid probes (e.g., DNA and/or oligonucleotide probes) on a solid support, in particular onto silane coated solid substrates. Such methods can deliver nano to pico-liter size droplets with sub-millimeter spacing. Because the aqueous droplets are well defined on such a hydrophobic surface, it is possible to create an array with a high density of nucleic acid probes (e.g., DNA and/or oligonucleotide probes). Thus, it is possible to create arrays having greater than about 10,000 probe droplets/$cm^2$. Such arrays can be assembled through the use of a robotic liquid dispenser (such as an ink-jet printing device controlled by a piezoelectric droplet generator). Methods and apparatuses for dispensing small amount of fluids using such ink-jet printing techniques and piezoelectric ink-jet depositions have been previously described by Wallace et al. (U.S. Pat. No. 4,812,856), Hayes et al. (U.S. Pat. No. 5,053,100), both of which are herein incorporated by reference in their entirety. The array can also be created by means of a "gene pen". A "gene pen" refers to a mechanical apparatus comprising a reservoir for a reagent solution connected to a printing tip. The printing tip further comprises a means for mechanically controlling the solution flow. A multiplicity of "gene pens" or printing tips may be tightly clustered together into an array, with each tip connected to a separate reagent reservoir or discrete "gene pens" may be contained in an indexing turntable and printed individually. Alternatively, the array can be created with a manual delivery system, such as a pipetman. Because these arrays are created with a manual delivery system, these arrays will generally not be as complex as those created with an automated delivery system. Arrays created with a manual delivery system will typically be spaced further apart. Preferably, arrays created with a manual delivery system will be created in a 96-well or 384-well plate.

Unlike traditional techniques, the present invention does not require the use of expensive crosslinking agents, which are typically very difficult to use and quite sensitive to air and humidity. Instead nucleic acid probes (e.g., DNA and/or oligonucleotide probes) are directly attached to the multiamino organosilane coated glass structure. Crosslinking agents bearing two different reactive functional groups are known as heterobifunctional crosslinkers, and the two functional groups are reactive toward different and distinct chemical moieties, typically thiols, hydroxyls, benzylhalides and amines. One advantage of the present invention is that a heterobifunctional crosslinking agent is not needed, allowing for a more efficient and inexpensive method for array preparation, particularly large scale preparation.

Methods which have been employed for the attachment of preformed synthetic or naturally occurring nucleic acids (e.g., DNA or oligonucleotides) to solid surfaces for the above mentioned applications and on the aforementioned substrates can be used: heat treatment, electrodeposition, UV crosslinking, (nitrocellulose, nylon); electrostatic, covalent linking, and exploitation of strong intermolecular ligand/receptor binding as for enzyme- or protein-linked affinity methods.

A preferred use of the modified substrates of the present invention is for creating DNA microarrays. Arrays are generally comprised of known, single-stranded nucleic acid fragments (e.g., SNP; probes) that are attached to a solid support in known locations (see FIG. 1). The DNA microarray is generally used as a tool for identifying unknown, single-stranded cDNA fragments (targets) that exist in a buffered solution. These targets are often formed during expression analysis or SNP detection experiments, and are tagged with a fluorescent dye for identification purposes.

The unknown targets are identified using a hybridization experiment, whereby a DNA microarray (containing the probes) and a buffered solution (containing the targets) are combined (see FIG. 1). When combined, complimentary probes and targets hybridize, forming chemically stable, hydrogen bonded double stranded DNA at specific locations on the microarray. The hybridized microarray is then rinsed and analyzed with a fluorescent scanner to semi-quantitatively determine the identity and concentration of target probes produced during the expression analysis or SNP detection experiment. FIG. 1 is a pictorial representation of the typical steps that are involved with DNA microarray experiment. A DNA chip containing known DNA fragments (probes) at known locations (a) is introduced to a solution containing fluorescently tagged, unknown DNA (targets), (b) hybridization occurs between complimentary DNA fragments, (c) and a scanner is then used to determine the identity and quantity of unknown DNA (d).

Although fluorescence is a preferred method, any method of determining the analytical output can be used. A label, tag, radioisotope, molecule, or any substance which emits a detectable signal or is capable of generating such a signal, e.g., luminescence enzyme, or any of the variety of known signaling entities are contemplated.

In a preferred embodiment, the analytical output is obtained by fluorescent spectroscopic methods using fluorescent dyes. Use of a wide variety of fluorescence detection methods is contemplated. The fluor (fluorescent dye) is coupled directly to the pyrimidine or purine ring of the nucleotides of the probe{Ried, T. et al. (Proc. Natl. Acad. Sci. (U.S.A.) 89:1388–1392 (1992), herein incorporated by reference}; U.S. Pat. Nos. 4,687,732; 4,711,955; 5,328,824; and 5,449,767, each herein incorporated by reference. Alternatively, the fluor may be indirectly coupled to the nucleotide as for example, by conjugating the fluor to a ligand capable of binding to a modified nucleotide residue. The most common fluorescent dyes used for DNA microarray applications are Cy3™ and Cy5™. The Cy3™ absorption and emission windows are centered at 550 nm and 570 nm, respectively, while the Cy5™ absorption and emission windows are centered at 649 nm and 670 nm, respectively. The absorption and emission spectra for Cy3™ and Cy5™ dyes are shown in FIG. 2. FIG. 2 further depicts plots of the emission spectra for Cy3™, Cy5™ and FluorX™. Although Cy3™ and Cy5™ are the most common fluors, other fluors can be used such as 4'-6-diamidino 2-phenyl indole (DAPI), fluorescein (FITC), and the new generation cyanine dyes Cy3.5, Cy5.5 and Cy7. Of these Cy3, Cy3.5, Cy5 and Cy7 are particularly preferred. The absorption and emission maxima for the respective fluors are: DAPI (Absorption maximum: 350 nm; Emission maximum: 456 nm), FITC (Absorption maximum: 490 nm; Emission maximum: 520 nm), Cy3 (Absorption maximum: 554 nm; Emission maximum: 568 nm), Cy3.5 (Absorption maximum: 581 nm; Emission maximum: 588 nm), Cy5 (Absorption maximum: 652 nm; Emission maximum: 672 nm), Cy7 (Absorption maximum: 755 nm: Emission maximum: 778 nm). Complete properties of selected fluorescent labeling reagents are provided by Waggoner, A. (Methods in Enzymology 246:362–373 (1995) herein incorporated by reference). In light of the above, it is readily apparent that other fluorophores having adequate spectral resolution can alternatively be employed in accordance with the methods of the present invention.

The disclosures of U.S. Pat. Nos. 5,348,853; 5,119,801; 5,312,728; 5,962,233; 5,945,283; 5,876,930; 5,723,591; 5,691,146; and 5,866,336 disclosing fluorophore labeled oligonucleotides are incorporated herein by reference. Guidance for making fluorescent intensity measurements and for relating them to quantities of analytes is available in the literature relating to chemical and molecular analysis, e.g. Guilbault, editor, Practical Fluorescence, Second Edition (Marcel Dekker, New York, 1990); Pesce et al, editors, Fluorescence Spectroscopy (Marcel Dekker, New York, 1971); White et al, Fluorescence Analysis: A Practical Approach (Marcel Dekker, New York, 1970); and the like.

As mentioned above, the improved DNA adhesion realized with a multiamino organosilane on a borosilicate glass can be further improved by first coating with $SiO_2$ or alternatively leaching the surface with an acid and heat treating. Table I shows that the best percent DNA retention values were realized with DETA-coated $SiO_2$. Although this result is encouraging, the price of synthetic $SiO_2$ substrates can be prohibitively high for DNA microarraying applications. The excellent DNA retention achieved with $SiO_2$ is likely due to the concentration, spatial distribution and acid constant of the Si—OH groups that are available at the $SiO_2$ glass surface, which can be used for multiamino organosilane attachment. For example, a large Si—OH concentration at the surface of synthetic $SiO_2$ can result in a higher concentration of multiamino organosilane attachment per unit area, and more multiamino organosilane per unit area then results in a greater active site density and affinity for DNA probe adhesion. FIG. 5 shows the covalent attachment of a 3-mer oligonucleotide to DETA molecules on the glass surface. Ionic bonding between the phosphate backbone of the oligonucleotide and amine groups is depicted on the left. While covalent bonding between the thymidine residue on the oligonucleotide and the alkyl group of the DETA molecule induced by UV irradiation and/or heat treatment is shown on the right.

DNA retaining glass spheres (microspheres) (1 mm to 1000 mm) prepared by flame spheroidizing crushed borosilicate 1, borosilicate 2, borosilicate 3 or $SiO_2$ are optionally coated with $SiO_2$ or acid leached and there after coated with a multiamino organosilane to obtain tiny glass vehicles that are capable of retaining high concentrations of nucleic acid probes.

Substrates of the present invention have numerous uses including "adhesive scaffolds," upon which tissue engineering could be conducted; in DNA hybridization analysis to detect or identify a genetic target such as a specific nucleic acid sequence, microorganism, genetic disorder etc.; to obtain patterns or arrays of nucleic acids that may be non-covalently or covalently bound to the substrate. Handling conditions and reagents should be chosen such that they are not destructive to the underlying multiamino organo silane coating to the substrate, and to promote maximum density of biomolecules attached to the substrate.

Having described the invention, the following examples are given to illustrate specific applications of the invention including the best mode now known to perform the invention. These specific examples are not intended to limit the scope of the invention described in this application. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above or below, is hereby incorporated by reference.

EXAMPLES

Example I

FIG. 3 shows Self-fluorescence for various DETA-coated glasses measured under Cy3™ (top) and Cy5™ (bottom) excitation and emission conditions. Data obtained from commercially available Corning CMT Gaps and Telechem Super Amine substrates are also shown. All relative fluorescence values were corrected for thickness by dividing by the output value from an Axon GenePix scanner by the thickness of the respective substrate in mm. All scans are obtained at 100% laser power and PMT tube gain of 700 using an Axon GenePix Pro 3 scanner. Nominal standard deviations are ±4%. A=$SiO_2$, B=Borosilicate 1, C=Borosilicate 3, D=Borosilicate 2

Example II

1) Borosilicate #1 Glass (Nominal Thickness 1.1 mm)

| Oxide Component | Input Content (wt %) |
|---|---|
| $SiO_2$ | 58–85 |
| $B_2O_3$ | 7–15 |
| $Al_2O_3$ | 0–8 |
| $Na_2O$ | 0–15 |
| $K_2O$ | 0–8 |
| ZnO | 0–8 |
| CaO | 0–8 |
| MgO | 0–8 |
| $As_2O_3$ | 0–2 |
| $Sb_2O_3$ | 0–2 |

2) Borosilicate #2 Glass (Nominal Thickness 1.1 mm)

| Oxide Component | Input Content (wt %) |
|---|---|
| $SiO_2$ | 40–60 |
| $B_2O_3$ | 10–20 |
| $Al_2O_3$ | 8–20 |
| BaO | 20–30 |
| $Na_2O$ | 0–5 |
| $K_2O$ | 0–5 |
| ZnO | 0–7 |
| CaO | 0–8 |
| MgO | 0–5 |
| $As_2O_3$ | 0–2 |
| $Sb_2O_3$ | 0–2 |

3) Borosilicate #3 Glass (Nominal Thickness 1.1 mm)

| Oxide Component | Input Content (wt %) |
|---|---|
| $SiO_2$ | 60–70 |
| $B_2O_3$ | 5–10 |
| $Al_2O_3$ | 0.1–8 |
| $Na_2O$ | 0–8 |
| $K_2O$ | 0–8 |
| ZnO | 3–10 |
| $TiO_2$ | 1–10 |
| CaO | 0–5 |
| MgO | 0–5 |
| $As_2O_3$ | 0–2 |
| $Sb_2O_3$ | 0–2 |

4) Soda Lime Silicate #1 (Nominal Thickness 1.0 mm)

| Oxide Component | Input Content (wt %) |
|---|---|
| $SiO_2$ | 65–75 |
| $Na_2O$ | 5–15 |
| $K_2O$ | 5–15 |
| ZnO | 2–6 |
| $TiO_2$ | 0.1–5 |
| BaO | 0.1–5 |
| CaO | 0–10 |
| MgO | 0–6 |
| PbO | 0–3 |
| $Al_2O_3$ | 0–3 |
| $B_2O_3$ | 0–5 |
| $As_2O_3$ | 0–2 |
| $Sb_2O_3$ | 0–2 |

5) Synthetic Fused Silica ($SiO_2$) (Nominal Thickness 2.3 mm)

borosilicate 1, borosilicate 2, borosilicate 3, soda-lime silicate 1 and $SiO_2$ glasses are each coated with DETA without optimizing any of the parameters (i.e., no effort is made to optimize the solution pH, wt % of DETA in solution, chemical composition of the DETA containing solution, post coating heat-treatment, etc.) The DETA samples are characterized for performance by measuring the self-fluorescence and the DNA retention, as described below.

SiO2 69.4
Na2O 8.1
K2O 8.4
CaO 7.2
BaO 2.1
ZnO 4.1
TiO2 03
Sb2O3 0.4

Self-Fluorescence:

The main contribution to self-fluorescence during a DNA microarray experiment generally results from the solid support, which is often comprised of a coated or un-coated glass. Various coated glasses were measured for low self-fluorescence (with respect to the self-fluorescence measured for Corning CMT-Gaps™ and Telechem, Inc. Super Amine™ coated substrates that are commonly used for DNA microarray applications) for the Cy3™ and Cy5™ absorption and emission windows.

The glass types utilized for the self-fluorescence study are borosilicate 1, borosilicate 2, borosilicate 3 and $SiO_2$. The first three glasses are multi-component oxide silicate glasses that are produced in a thin, flat format that is suitable for DNA microarray applications. $SiO_2$ is an extremely pure glass produced by a chemical vapor deposition technique, which exhibits low self-fluorescence. $SiO_2$ must be cut, ground and polished to obtain a substrate suitable for DNA microarray applications. The self-fluorescence of commercially available Corning CMT GAP and TeleChem Arraylt slides is also measured for comparative purposes.

The various glasses described above are scanned for self-fluorescence before and after being coated with DETA, using a green (523 nm, for Cy3™ excitation) and red (635 nm, for Cy5™ excitation) laser using a GenePx 4000A fluorescent scanner. All background readings are scanned at 100% laser power and at constant sensitivity (photomultiplier tube gain; PMT=700). Using an Axon GenePix Pro 3 scanner and software package. Fluorescence intensities for each of the coated glasses are calculated on a relative scale and normalized for thickness (i.e., the relative fluorescent value is divided by the thickness of the glass, nominal thickness of $SiO_2$=2.3 mm, borosilicate 1=1.2 mm, borosilicate 2=1.1 mm, and borosilicate 3=1.1 mm). There was no statistically significant difference for the self-fluorescence data obtained before and after coating with DETA, thus the glass substrate is primarily responsible for self fluorescence. FIG. 3 shows the relative self-fluorescence values for the various DETA-coated glasses. Data from commercially available Corning CMT-Gaps and TeleChem Arraylt (amino propyl silane coated) substrates are also shown in FIG. 3. All relative fluorescence values are corrected for thickness by dividing by the output value from the Axon GenePix scanner by the thickness of the respective substrate in mm. Nominal standard deviations are ±4%.

Example III

DNA Retention

A semi-quantitative DNA retention test is used to quantify the extent of chemical bonding between DNA probes and a coated glass surface, as described below (also see FIG. 4). Nucleic acid probes (450 nucleotides in length) are tagged with Cy3™ fluorescent dye by a conventional PCR reaction. The tagged DNA probes are then suspended (1 microgram per microliter, or about 3.4 micromolar) in 3X saline sodium citrate buffer (450 mM NaCl, 45 mM sodium citrate, pH=7.0). A mechanical, "Stanford-type microarrayer" built by the Penn State Engineering Services is then used to dispense spots that are 0.160 mm in diameter in triplicate onto a coated glass substrate. A total of six spots are used for each DNA retention experiment. The spotted substrates are scanned in the as-printed state (after air-drying) to obtain an initial value for fluorescence. At the time of this first fluorescence scan, the probes are only attached to the coated substrate by relatively weak ionic interactions. To obtain strong, covalent chemical bonding, the spotted substrates are hydrated and UV crosslinked to the coated substrate. Hydration is achieved by placing them array side down over a chamber of boiling $H_2O$ for 2–10 sec to assure each spot has absorbed water. The hydrated spotted substrates are then dried at 80C. Finally, the DNA probes are UV cross-linked to the surface of the coated substrate using a Stratalinker UV crosslinker, (Stratagene, LaJolla, Calif.) at 190 mJ.

After the UV crosslinking step, the spotted substrates are subjected to a vigorous washing process that is intended to remove probes that are not covalently bonded to the coated glass substrate. This process consists of:

Immersing the spotted substrates in 0.1 mild detergent (SDS) for 30 sec, then in water for 30 sec, then boiling in $H_2O$ for 3 min, and in 70% EtOH for 2 min. Spin drying at 500 rpm for 5 min.

After the vigorous washing process, the spotted substrates are scanned again for fluorescence, and the percent DNA retention is calculated by comparing changes in the fluorescence intensity of the spots from the as-printed state to the post-cleaning/boiling state. Reported DNA retention values are based on the average of three separate experiments to ensure statistical integrity.

Table I lists the percent DNA retention values for the various multi component oxide silicate glasses that are coated with DETA and APS. A DETA-coated glass exhibits significantly higher DNA retention than the same glass that is coated with APS. When borosilicate 1 and borosilicate 2 are coated with DETA they exhibit DNA retention that is 60% higher than that realized when coating with APS. $SiO_2$ coated with DETA exhibited the largest average percent DNA retention of 22.5%, 12% higher than DETA coated borosilicate 2 and 17% higher than DETA-coated borosilicate 1.

Example IV

Silica coatings have been achieved on borosilicate 1 and borosilicate 2 surfaces, using the following technique. Silica surfaces are prepared under ambient conditions onto glass substrates by applying tetraethylorthosilicate (TEOS) with a spin coater. The substrates are first cleaned according to the standard cleaning protocol, described previously. The rotation speed for the coating is 2500 rpm. Approximately 2.5 ml of sol-gel solution is used for each slide. The aged sol-gel solution is applied to the slide surface under constant spinning, by drop wise injection through a disposable syringe. A 0.2 mm Milipore filter is used to filter agglomerates and achieve a uniform coating. After spin coating the sol-gel, the substrates are spun for an additional 15 sec. to achieve complete drying and coverage.

After spin coating, samples are baked at 120° C. for 30 min to remove physically attached components ($H_2O$, EtOH). Some samples are also baked at about 450° C. to remove all the organic components. These samples are kept in the oven during cooling to avoid crack formation in the $SiO_2$ films. Finished samples are kept in desiccator. Around 90–95% surface coverage can be achieved by spin coating. $SiO_2$-coated slides are treated with two different silane solutions 5 wt. % APS and DETA, then agitated for 5 min in MeOH, rinsed for 10 min with DI water, dried with purified $N_2$ gas, then baked at 110° C./15 min and 120° C./5 min for APS and DETA coated samples, respectively.

Example V

Borosilicate 1, borosilicate 2, borosilicate 3 and $SiO_2$ glass substrates can be coated with DETA to achieve a surface that is optimal for DNA adhesion. The following process is generally used to coat the various glasses with DETA.

General Glass Cleaning and Coating Protocol

1. Agitate glass slides in 1–70 wt % $NaOH_{(aq)}$ solution for 0.1 to 24 hrs. (4–95° C.)
2. Sonicate in doubly distilled (dd) $H_2O$ for 0.1 to 24 hrs. (4–95° C.)
3. Agitate slides in 0.1–70 wt % $HCl_{(aq)}$ for 0.1 to 24 hrs (4–95° C.)
4. Sonicate in dd $H_2O$ for 0.1 to 24 hrs. (4–95° C.)
5. Shake in ultra-pure, low residue methanol for 0.1 to 24 hrs. (4–30° C.)
5a- An optional coating step can be inserted here, whereby the glass surface is coated with $SiO_2$ (See example IV). This coating step could be accomplished by the chemical vapor deposition of $SiO_2$, the sputtering of $SiO_2$, mist deposition with an aerosol, and/or the liquid phase deposition or dip coating of $SiO_2$ via a sol gel technique. The sol gel coatings can be deposited from both acidic and basic solutions to influence the pore size and specific surface area of the deposited silica. In the case of the TEOS/aminosilane mixtures, the pH also influences the orientation and conformation of the silane molecules on the surface. The drying conditions can be varied from air to nitrogen to influence carbomide formation.
6. Shake in DETA (0.1 to 20 wt %) solution for 1–60 min. The solution can contain 0.1 to 99.9 wt % of $H_2O$ and 5 to 99.9 wt % of an organic solvent or solvents, including acetone, methanol, ethanol, or toluene. Acetic acid may be used to adjust pH of an aqueous solution, but the DETA solution is generally maintained at a pH>10 for glass substrate coating applications.
7. Shake in ultra-pure, low residue methanol again for 0.1 to 24 hours.
8. Rinse well with dd $H_2O$ for 0.1 to 24 hours.
9. Spin dry for 5 min. at 500 rpm (Class-100 clean room is optional)
10. Heat treat the coated samples at a temperature ranging from 80 to 250C. for 0.1 to 24 hours. (Class-100 clean room is optional)
11. Store in vacuum desiccator.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

TABLE I

Percent DNA Retention for Various Glasses Coated with APS or DETA*

| Glass | APS | DETA |
|---|---|---|
| BOROSILICATE 1 | 12.0 | 19.2 |
| BOROSILICATE 2 | 12.6 | 20.1 |
| BOROSILICATE 3 | 9.9 | 13 |
| $SiO_2$ | nm | 22.5 |

*Typical standard deviations were 3%, nm = not measured

What is claimed is:

1. A substrate for attachment of biomolecules comprising:
a low self-fluorescence glass substrate having an acid leached surface coated thereover with a multiamino organo silane.

2. A substrate according to claim 1, wherein the multiamino organosilane is trimethoxysilylpropyl-diethylenetriamine.

3. An array of immobilized biomolecules comprising a plurality of biomolecules attached to a substrate according to claim 1.

4. An array according to claim 3, wherein the biomolecules are DNA, unmodified nucleic acid, antibodies, antigens, proteins, or oligonucleotides.

5. A substrate according to claim 1, wherein the substrate is a low self-fluorescent multi-oxide component glass.

6. A substrate according to claim 1, wherein the multiamino organosilane is a multiamino alkyl monoalkoxy silane, multiamino alkyl dialkoxy silane, and/or a multiamino alkyl trialkoxy silane.

7. A substrate according to claim 1, wherein the multiamino organosilane is trimethoxysilylpropyl-diethylenetriamine (DETA), N-(2-aminoethyl)-3-aminopropyltrimethoxysilane (EDA), and/or (aminoethyl aminomethyl)phenethyltrimethoxysilane (PEDA).

8. A substrate according to claim 1, wherein low self-fluorescent multi-oxide component glass is soda-lime glass or borosilicate.

9. An array of immobilized nucleic acid molecules comprising a plurality of nucleic acid molecules attached to a substrate according to claim 1.

10. A method of performing a hybridization assay comprising incubating target nucleic acid molecules with a substrate according to claim 9.

11. A method of performing a hybridization assay comprising incubating target nucleic acid molecules with a substrate according to claim 10, wherein the biomolecules are nucleic acid oligomers.

12. A method of attaching biomolecules to a low self-fluorescent substrate comprising:
acid leaching a low self-fluorescent borosilicate or soda lime silicate glass substrate, thereafter applying a coating of a multiamino organo silane, and bonding biomolecules thereto.

13. A method according to claim 12, wherein the multiamino organosilane is a multiamino alkyl monoalkoxy silane, multiamino alkyl dialkoxy silane, and/or a multiamino alkyl trialkoxy silane.

14. A method according to claim 12, wherein the multiamino organosilane is trimethoxysilylpropyl-diethylenetriamine (DETA), N-(2-aminoethyl)-3aminopropyltrimethoxysilane (EDA), and/or (aminoethyl aminomethyl)phenethyltrimethoxysilane (PEDA).

15. A method according to claim 12, wherein the attachment of biomolecules create an array of immobilized nucleic acid molecules.

16. A substrate for attachment of biomolecules comprising a low fluorescent glass coated with a multiamino organosilane wherein said glass comprises, in % by weight on an oxide basis:
$SiO_2$ 58–55,
$B_2O_3$ 7–15,
$Al_2O_3$ 0–8,
$Na_2O$ 0–15,
$K_2O$ 0–8,
ZnO 0–8,
CaO 0–8,
MgO 0–8,
$As_2O_3$ 0–2,
$Sb_2O_3$ 0–2.

17. A substrate according to claim 16, wherein the multiamino organosilane is a multiamino alkyl monoalkoxy silane, multiamino alkyl dialkoxy silane, and/or a multiamino alkyl trialkoxy silane.

18. A substrate according to claim 16, wherein the multiamino organosilane is trimethoxysilylpropyl-diethylenetriamine (DETA), N-(2-aminoethyl, 3-aminopropyltrimethoxysilane (EDA), and/or (aminoethyl aminomethyl)phenethyltrimethoxysilane (PEDA).

19. A substrate for attachment of biomolecules comprising a low fluorescent glass coated with a multiamino organosilane wherein said glass comprises, in % by weight on an oxide basis:
$SiO_2$ 40–60
$B_2O_3$ 10–20
$Al_2O_3$ 8–20
BaO 20–30
$Na_2O$ 0–5
$K_2O$ 0–5
ZnO 0–7
CaO 0–8
MgO 0–5
$As_2O_3$ 0–2
$Sb_2O_3$ 0–2.

20. A substrate for attachment of biomolecules comprising a low fluorescent glass coated with a multiamino organosilane wherein said glass comprises, in % by weight on an oxide basis:
$SiO_2$ 60–70
$B_2O_3$ 5–10
$Al_2O_3$ 0.1–8
$Na_2O$ 0–8
$K_2O$ 0–8
ZnO 3–10
$TiO_2$ 1–10
CaO 0–5
MgO 0–5
$As_2O_3$ 0–2
$Sb_2O_3$ 0–2.

21. An array of immobilized nucleic acid molecules comprising a plurality of nucleic acid molecules attached to a substrate according to claim 20.

22. A method of performing a hybridization assay comprising incubating target nucleic acid molecules with a substrate according to claim 21.

23. A substrate for attachment of biomolecules comprising a low fluorescent glass coated with a multiamino organosilane wherein said glass comprises, in % by weight on an oxide basis:
$SiO_2$ 65–75
$Na_2O$ 5–15
$K_2O$ 5–15
ZnO 2–6
$TiO_2$ 0.1–5
BaO 0.1–5
CaO 0–10
MgO 0–6
PbO 0–3
$Al_2O_3$ 0–3
$B_2O_3$ 0–5
$As_2O_3$ 0–2
$Sb_2O_3$ 0–2.

24. A substrate for attachment of biomolecules comprising:
a low fluorescent glass having
a first coating of $SiO_2$ and thereover a coating of an amino silane wherein said glass comprises, in % by weight on an oxide basis:
$SiO_2$ 60–70
$B_2O_3$ 5–10
$Al_2O_3$ 0.1–8
$Na_2O$ 0–8
$K_2O$ 0–8
ZnO 3–10
$TiO_2$ 1–10
CaO 0–5
MgO 0–5
$As_2O_3$ 0–2
$Sb_2O_3$ 0–2.

25. A substrate according to claim 24, wherein said amino silane is aminopropyl silane.

26. A substrate according to claim 25, wherein said amino silane is an aminopropyl trialkoxy silane, aminobutyldimethylmethoxysilane.

27. A substrate according to claim 24, wherein said amino silane is gamma-3-amino propyl triethoxy silane, and/or 3-amino propyl trimethoxy silane.

* * * * *